US006743912B2

(12) United States Patent
Böttcher et al.

(10) Patent No.: US 6,743,912 B2
(45) Date of Patent: Jun. 1, 2004

(54) STORAGE AND TRANSPORTATION OF N-VINYL-EPSILON-CAPROLACTAM

(75) Inventors: Arnd Böttcher, Frankenthal (DE); Rolf Pinkos, Bad Dürkheim (DE); Rudolf Erich Lorenz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 40 days.

(21) Appl. No.: 10/033,914

(22) Filed: Jan. 3, 2002

(65) Prior Publication Data

US 2002/0091255 A1 Jul. 11, 2002

(30) Foreign Application Priority Data

Jan. 10, 2001 (DE) ......................................... 101 00 752

(51) Int. Cl.$^7$ ............................................ C07D 201/18
(52) U.S. Cl. ..................................................... 540/485
(58) Field of Search ......................................... 540/485

(56) References Cited

U.S. PATENT DOCUMENTS

| 3,377,340 A | 4/1968 | Hartwimmer et al. ...... 260/239 |
| 4,649,174 A | 3/1987 | Akiyama et al. ........... 524/841 |
| 6,147,145 A | 11/2000 | Aumüller et al. ............. 524/86 |

FOREIGN PATENT DOCUMENTS

| DE | 111 11 193 | 7/1961 |
| DE | 199 06 316 | 8/2000 |
| DE | 101 21 976 | 11/2001 |
| WO | WO 96/11217 | 4/1996 |

OTHER PUBLICATIONS

Ullmanns Encyklopädie der Technischen Chemie Band 23 (1983) pp. 610–615.
Ullmann's Ency. der Tech. Chem, Band 23, 611–614, 1983.

*Primary Examiner*—Bruck Kifle
(74) *Attorney, Agent, or Firm*—Keil & Weinkauf

(57) ABSTRACT

A method of storing and transporting N-vinyl-ε-caprolactam is provided wherein the N-vinyl-ε-caprolactam is kept in the liquid phase.

8 Claims, No Drawings

STORAGE AND TRANSPORTATION OF N-VINYL-EPSILON-CAPROLACTAM

The present invention relates to a method of storing and transporting N-vinyl-ε-caprolactam.

N-Vinyl-ε-caprolactam is used inter alia as a monomer unit in oligomers, polymers and copolymers. Thus it finds its way, for example, into the manufacture of paper coatings, adhesives, printing inks, detergents, engine oil additives, textile auxiliaries, radiation-curing surface coatings, cosmetics, pharmaceuticals, auxiliaries for petroleum production or chemicals for photographic applications.

N-Vinyl-ε-caprolactam is generally manufactured industrially by the addition of ethyne onto caprolactam and is described for example in Ullmanns Encyclopedia of Industrial Chemistry, ed. Bartholomé et al., volume 23, 4th edition, Weinheim 1983, pages 611 to 614. The synthesis is conventionally followed by a distillative purification, in which the product can be obtained in high purity by condensation from the gas phase. To suppress unwanted reactions such as decomposition, oligomerization or polymerization during storage and transportation, a stabilizer is conventionally added. A frequently used stabilizer is N,N'-bis(1-methylpropyl)-1,4-phenylenediamine, which is marketed by BASF AG under the trade name Kerobit® BPD. Examples of other known stabilizers are alkali metal hydroxides or phenothiazine derivatives.

For applications where the inherent color of the product should be minimal, for example in the cosmetic or photographic sector or in paper coatings, there is a need not only for a high chemical purity but also for a very high purity in respect of color-causing impurities. A few ppb by weight of color-causing impurities are generally sufficient to cause pronounced discoloration of the product.

N-Vinyl-ε-caprolactam obtained after distillation, normally with a stabilizer added, is conventionally transferred in the liquid state to containers such as bottles, drums or freight containers and is stored and transported at ambient temperature. Because of its melting point of 35° C., N-vinyl-ε-caprolactam solidifies shortly after transfer. The solid mass is conventionally remelted before the containers are emptied. It was recognized according to the invention that the melted product had a markedly darker yellowish to brownish color than the original product.

This undesired color change is referred to below as discoloration.

It is an object of the present invention to provide a method of storing and transporting N-vinyl-ε-caprolactam which no longer has the disadvantages described above, said N-vinyl-ε-caprolactam exhibiting only a very low tendency to discolor, even after prolonged storage and transportation for several months.

Surprisingly, we have found that this object is achieved by a method of storing and transporting N-vinyl-ε-caprolactam wherein the N-vinyl-ε-caprolactam is kept in the liquid phase.

The liquid phase is generally also referred to as the "melt". In the method according to the invention, it can also be interspersed with solid particles such as crystals of N-vinyl-ε-caprolactam. Moreover, solid particles such as crystals of N-vinyl-ε-caprolactam can be present, for example, as a sediment. In the method according to the invention, preferably the bulk of the N-vinyl-ε-caprolactam to be stored or transported is kept in the liquid phase. Particularly preferably more than 90% by weight, very particularly preferably more than 99% by weight and especially the whole of the N-vinyl-ε-caprolactam is kept in the liquid phase. Normally, the higher the proportion of liquid phase relative to any solid phase present, the lower is the tendency to discolor.

To keep the product in the liquid phase, the temperature used generally corresponds to the melting point or is above the melting point. Pure N-vinyl-ε-caprolactam has a melting point of 35° C. In the method according to the invention, the N-vinyl-ε-caprolactam is kept at a temperature preferably of 35 to 100° C., particularly preferably of 35 to 75° C. and very particularly preferably of 35 to 60° C.

The duration of storage and transportation in the method according to the invention is generally a few hours to several months. It can also be shorter or longer where appropriate. The duration is preferably at least three days, particularly preferably at least five days and very particularly preferably at least seven days.

Stabilizers can be added to the N-vinyl-ε-caprolactam used in the method according to the invention in order to suppress unwanted reactions such as decomposition, oligomerization or polymerization. Examples of suitable stabilizers which may be mentioned are N,N'-bis(1-methylpropyl)-1,4-phenylenediamine, which is marketed by BASF AG under the trade name Kerobit® BPD, alkali metal hydroxides or phenothiazine derivatives. If stabilizers are added to the N-vinyl-ε-caprolactam, their content is generally 1 to 1000 ppm by weight, preferably 1 to 100 ppm by weight and particularly preferably 5 to 50 ppm by weight.

The N-vinyl-ε-caprolactam used in the method according to the invention generally has a purity of over 98% by weight, preferably of over 99% by weight and particularly preferably of over 99.5% by weight. The remainder to 100% by weight generally consists of unreacted caprolactam, added stabilizers or impurities such as those formed, for example, in the manufacture of the product or, for example, due to decomposition, oligomerization or polymerization. Normally the remainder consists predominantly of caprolactam.

In the method according to the invention, the N-vinyl-ε-caprolactam can be covered with a layer of various gases or contain various gases. Examples which may be mentioned are nitrogen, noble gases (e.g. argon) or air.

The product is generally stored and transported in containers. Their size is generally irrelevant as far as the method according to the invention is concerned. As a rule, containers in the liter and $m^3$ ranges are used. The geometric shape of the containers is also generally irrelevant as far as the method according to the invention is concerned. Preferred examples are: (i) substantially spherical containers (e.g. so-called spherical tanks), (ii) substantially cylindrical containers (e.g. bottles, drums, so-called cylindrical tanks or tank wagons) and (iii) substantially cuboid containers.

The walls of the container should be chemically inert to N-vinyl-ε-caprolactam and leaktight. Examples of suitable materials are iron, stainless steel or metal or plastic packing drums (e.g. made of polypropylene or polyethylene) painted on the inside.

In the method according to the invention, the N-vinyl-ε-caprolactam is preferably stored and transported in a thermally insulated container, this being understood as meaning a container which includes thermal insulation. Examples of suitable thermal insulators which may be mentioned are intermediate layers containing a vacuum, containing a gas with a low thermal conductivity, such as helium, or containing solid insulating materials such as foamed polystyrene (e.g. Styropor®) or glass or mineral wool.

When N-vinyl-ε-caprolactam is stored and transported in a thermally insulated container, it can be (i) packed directly without other containers, or (ii) packed in other containers.

Suitable examples of (i) which may be mentioned are thermally insulated tanks (e.g. spherical, cylindrical or wagon tanks) or thermally insulated drums. Suitable examples of (ii) which may be mentioned are thermally insulated freight containers (e.g. Iso freight containers), which contain the N-vinyl-ε-caprolactam in the form of other containers (e.g. drums or bottles).

In the method according to the invention, the N-vinyl-ε-caprolactam is particularly preferably stored and transported in a thermally insulated, heatable container, which is to be understood as meaning a container provided with a heater as well as the abovementioned thermal insulation. In the case of thermally insulated containers in which the N-vinyl-ε-caprolactam is (i) packed directly without other containers, the heater can take the form of, for example, heating elements located directly in the N-vinyl-ε-caprolactam to be stored or transported. Another possibility is, for example, for the heater to be located between the thermal insulation and the container lining. Examples which may be mentioned here are drums or tanks provided with a heating jacket. In the case of thermally insulated containers in which the N-vinyl-ε-caprolactam is (ii) packed in other containers, the heater is conventionally located inside these containers.

In one preferred embodiment of the method according to the invention, 220 l drums are stored or transported at 40° C. in a heatable Iso freight container.

The method according to the invention for storing and transporting N-vinyl-ε-caprolactam is particularly surprising because, according to the general state of the art, an appreciably greater reactivity is to be expected in the liquid and hence diffusion-mobile phase.

The preferred method according to the invention, wherein the N-vinyl-ε-caprolactam is kept at its melting point or above, is particularly surprising because, according to the general state of the art, the reactivity normally increases with temperature.

Neither the fact that the liquid product proves less reactive than the solid product in terms of the formation of color-causing impurities, nor the fact that this effect also holds for liquid product which is kept at a markedly higher temperature than the solid product, can be deduced from the general state of the art.

The method according to the invention makes it possible to store and transport N-vinyl-ε-caprolactam, leading to only a slight discoloration of the product, even after prolonged storage and transportation for several months.

EXAMPLES

To characterize the possible discoloration of the N-vinyl-ε-caprolactam, the color numbers were determined by the APHA method, analogously to DIN EN 1557.

Examples 1 and 2

500 g of liquid N-vinyl-ε-caprolactam with an APHA color number of 8 were transferred to each of two glass bottles and sealed.

In Comparative Example 1 the sample quickly solidified at an ambient temperature of approx. 25° C. and was stored in the solid state for 21 days at this temperature. The sample was then melted at about 50° C. and the APHA color number was determined again. It was 125.

In Example 2 the sample was stored in the liquid state at 50° C. and the APHA color number was then determined again. It was 24.

Examples 3 and 4

200 kg of liquid N-vinyl-ε-caprolactam with a purity of 99.8 GC area % and an APHA color number of 58 were transferred to each of two 220 l iron drums and sealed.

In Comparative Example 3 the sample quickly solidified at an ambient temperature of 20° C. and was stored in the solid state for 1 month at this temperature. The sample was then melted at about 50° C. and the APHA color number was determined again. It was 152.

In Example 4 the sample was stored in the liquid state at 40° C. and the APHA color number was then determined again. It was 84.

Examples 1 to 4 show that, compared with the N-vinyl-ε-caprolactam stored in the solid phase, the N-vinyl-ε-caprolactam stored in the liquid phase exhibits only an extremely low tendency to discolor. Thus, for instance, the color number in Example 4 according to the invention, where the N-vinyl-ε-caprolactam was stored in the liquid state for one month in a 220 l iron drum, increased by only 26 APHA units, whereas in Comparative Example 3, for storage in the solid phase, a markedly greater increase of 94 units was observed.

We claim:

1. A method of storing and transporting N-vinyl-ε-caprolactam, wherein the N-vinyl-ε-caprolactam is kept in the liquid phase.

2. A method as claimed in claim 1 wherein the N-vinyl-ε-caprolactam is kept at a temperature of 35 to 100° C.

3. A method as claimed in claim 1 wherein the N-vinyl-ε-caprolactam is kept at a temperature of 35 to 60° C.

4. A method as claimed in claim 1 wherein the N-vinyl-ε-caprolactam is stored or transported for a period of at least five days.

5. A method as claimed in claim 1 wherein the N-vinyl-ε-caprolactam is stored or transported for a period of at least seven days.

6. A method as claimed in claim 1 wherein N-vinyl-ε-caprolactam with a purity of over 98% by weight is used.

7. A method as claimed in claim 1 wherein the N-vinyl-ε-caprolactam is stored and transported in a thermally insulated container.

8. A method as claimed in claim 7 wherein the N-vinyl-ε-caprolactam is stored and transported in a heatable container.

* * * * *